Jan. 12, 1965 C. H. FISCHER Plant Pat. 2,465
GLADIOLUS PLANT
Filed Nov. 6, 1963
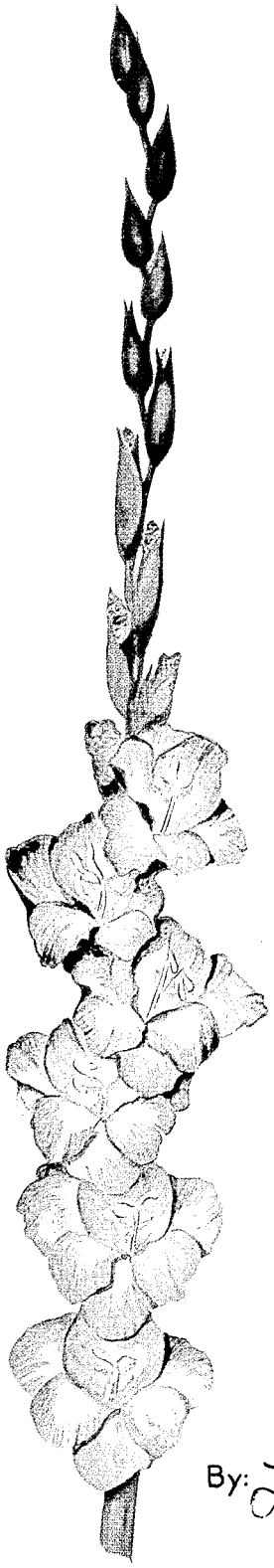
INVENTOR
CARL H. FISCHER
By: Lamont Johnston
ATTORNEY United States Patent Office Plant Pat. 2,465
Patented Jan. 12, 1965

2,465
GLADIOLUS PLANT

Carl H. Fischer, St. Charles, Minn., assignor to Selected Glads, Inc., New Albany, Ind., a corporation of Tennessee Filed Nov. 6, 1963, Ser. No. 321,987
1 Claim. (Cl. Plt.—85)

My present invention relates to a new and improved variety of gladiolus plant and is notable particularly for its blue color, clean, creamy-white throat, and small size. I have identified this new variety as seedling No. 93–54 in my breeding work.

To the best of my knowledge, this new variety is the result of a cross between the varieties Caribbean (Plant Patent No. 1,654) and an unnamed seedling (unpatented) whose parents were Rose O'Day and Elizabeth the Queen (both unpatented). Caribbean was the seed parent and the seedling was the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proven to be permanently fixed.

The illustration, made a part of this application, shows a single bloom spike of this new variety, reduced in size, and is as nearly true to color as it is possible to depict. The illustration shows the arrangement of the florets on the stem, the large white blotch and the predominating light blue color.

The color plate references, in the following detailed description, are to the "Horticultural Colour Chart," by the British Colour Council. Where there are other references to color, the ordinary dictionary meanings of the terms are intended.

*The Plant*

Growth: Vigorous: bloom spike averages 48 inches in height. Average propagator.

Blooming: The variety is an early bloomer, blooming in about 70 days from large bulbs. Each spike opens from six to seven 2¾ inch florets at one time. Successive blooms open, totalling an average of eighteen to twenty to each spike.

Stems: Willowy and whippy. Diameter at base is ½ inch.

Foliage: Plant is upright and foliage, excluding the flower spike, is about 32 inches tall.

Disease resistance: This variety has been found unusually resistant to Fusarium yellows, Sclerotina dry rot and Septoria leaf spot.

Corms: Round, well-husked; husk is quite heavy. Flesh is Lemon Yellow $4/_2$. Bulbs average 2½ inches in diameter from adult plants.

*The Flower*

Spike: The spike is willowy; has eighteen to twenty buds and opens six to seven florets at one time.

Bud:

*Size.*—Opening buds are 2 inches long.

*Opening.*—Six to seven open at one time with five in color.

Flower:

*Arrangement.*—Florets are informally placed on the spike and all face in the same direction.

*Size.*—Lower blooms average 2¾ inches across. Upper blooms are progressively smaller.

*Form.*—Florets are wide open and round as saucers.

*Keeping qualities.*—Opens and keeps well.

Petals:

*Shape.*—Petals are very round with a slight frill at the edges.

*Size.*—The three outer petals are 1¾ inches across; inner lip petals are 1¼ in. across and the top inner petal is 1½ to 1⅝ inches across.

*Aspect.*—Substance is heavy with a smooth surface and only a slight ruffle at the edges.

*Fragrance.*—None.

*Color.*—From the heart of the flower to the outside edges, the color is Hyacinth Blue shading from $40/_1$ to $40/_2$ to $40/_3$. Reverse of floret is $40/_2$. Color at calyx is Roseine Purple $629/_1$. The blotch on freshly opened floret is Mimosa Yellow $602/_3$ which lightens to a creamy white as it fades.

Reproductive organs:

*Stamens.*—Roseine Purple $629/_3$.

*Pistil.*—White.

*Comparisons*

My new variety doesn't resemble any existing variety. There is no variety in commerce that is miniature in size, light blue in color, with a large, creamy white throat.

Having thus disclosed my invention, I claim:

The new and distinct variety of gladiolus plant substantially as herein shown and described, characterized by its small size and blossoms of light blue color with creamy white throats.

No references cited.

ABRAHAM G. STONE, *Primary Examiner.*